US008900202B2

(12) United States Patent
Helmer et al.

(10) Patent No.: US 8,900,202 B2
(45) Date of Patent: Dec. 2, 2014

(54) DRIVE MECHANISM FOR DRUG DELIVERY DEVICES

(75) Inventors: Michael Helmer, Frankfurt am Main (DE); Claudia Matthias, Frankfurt am Main (DE); Peter Nober, Rommersheim (DE); Reza Shahbazfar, Wiesbaden (DE); Benjamin Schaefer, Bischoffen (DE); Leo Zeimetz, Büttelborn (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 316 days.

(21) Appl. No.: 13/500,416

(22) PCT Filed: Oct. 8, 2010

(86) PCT No.: PCT/EP2010/065096
§ 371 (c)(1),
(2), (4) Date: Sep. 17, 2012

(87) PCT Pub. No.: WO2011/042539
PCT Pub. Date: Apr. 14, 2011

(65) Prior Publication Data
US 2013/0023831 A1    Jan. 24, 2013

(30) Foreign Application Priority Data
Oct. 8, 2009   (EP) .................................... 09172507

(51) Int. Cl.
A61M 5/00    (2006.01)
A61M 5/315   (2006.01)
A61M 5/24    (2006.01)
A61M 5/31    (2006.01)

(52) U.S. Cl.
CPC ............. *A61M 5/31515* (2013.01); *A61M 5/24* (2013.01); *A61M 5/3146* (2013.01); *A61M 2005/2407* (2013.01); *A61M 2207/00* (2013.01)
USPC ......................................................... 604/208

(58) Field of Classification Search
CPC .................... A61M 5/31543; A61M 5/31551; A61M 5/31585; A61M 5/24; A61M 5/31525; A61M 5/315; A61M 5/31533

USPC .................................................. 604/207, 208
See application file for complete search history.

(56) References Cited

U.S. PATENT DOCUMENTS 2,895,474 A   7/1959  Reznek
6,196,999 B1  3/2001  Goethel et al.

FOREIGN PATENT DOCUMENTS

GB   2220143      1/1990
WO   2009/095332  *  8/2009

OTHER PUBLICATIONS

European Search Report for European App. No. 09172507, completed Mar. 23, 2010.
International Search Report for International App. No. PCT/EP2010/065096, completed Feb. 17, 2011.
International Preliminary Report on Patentability for for International App. No. PCT/EP2010/065096, completed Sep. 22, 2011.

* cited by examiner

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

The present invention relates to a drive mechanism for a drug delivery device for dispensing of a dose of a medicinal product, comprising: a holder for a product-containing cartridge, the cartridge having a piston slidably arranged therein in an axial direction, a piston rod to be operably engaged with the cartridge's piston for dispensing of a dose of the medicinal product, an adjusting assembly adapted to eliminate axial clearance between the piston and the piston rod, wherein the adjusting assembly comprises at least one radially extending spike element for mutually locking in position the piston and the piston rod irrespective of the relative distance between piston and piston rod.

11 Claims, 4 Drawing Sheets

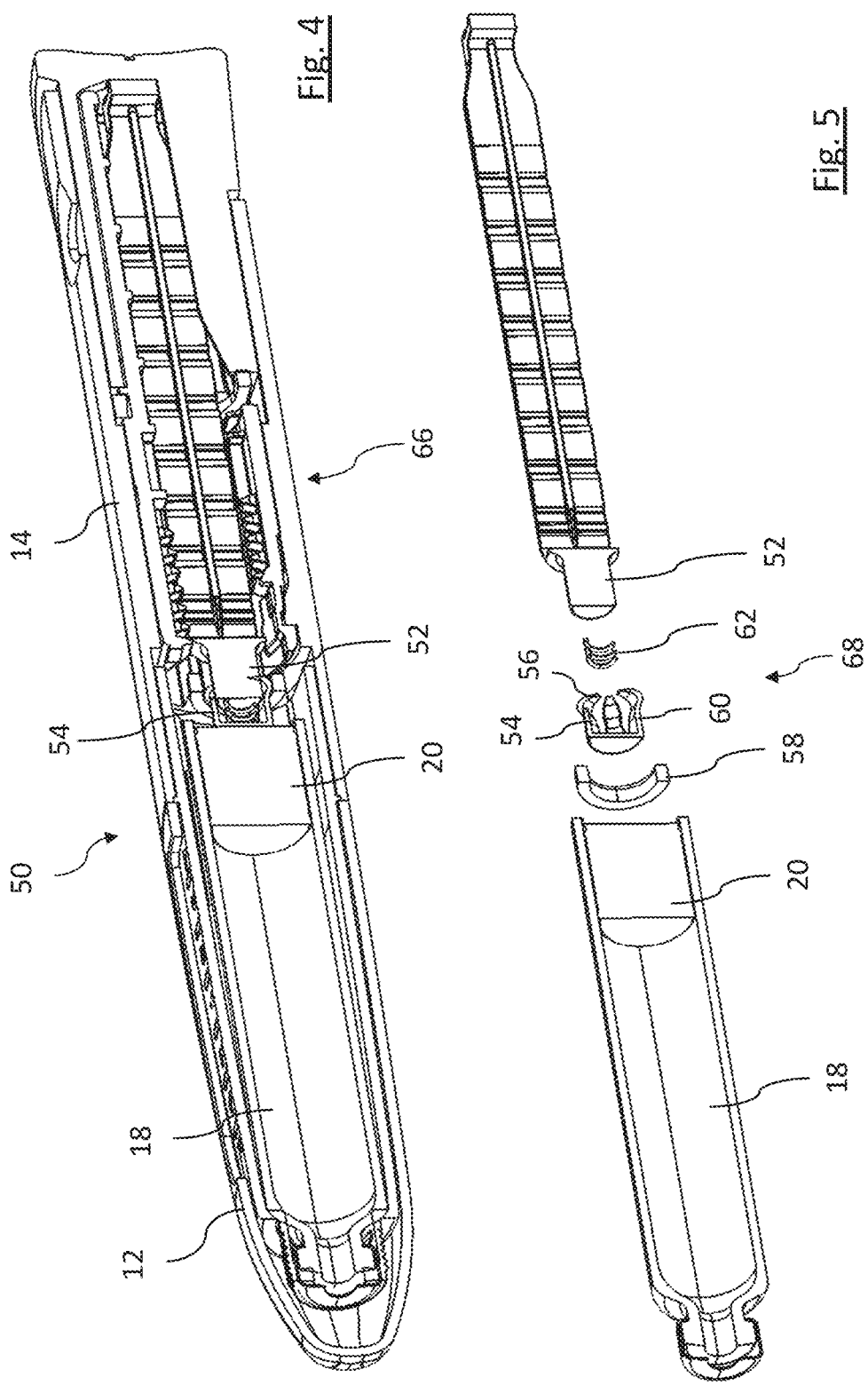

DRIVE MECHANISM FOR DRUG DELIVERY DEVICES

CROSS REFERENCE TO RELATED APPLICATIONS

The present application is a U.S. National Phase application pursuant to 35 U.S.C. §371 of International Application No. PCT/EP2010/065096 filed Oct. 8, 2010, which claims priority to European Patent Application No. 09172507.7 filed on Oct. 8, 2009. The entire disclosure contents of these applications are herewith incorporated by reference into the present application.

FIELD OF THE INVENTION

The present invention relates to a drive mechanism for a drug delivery device that allows a user to select single or multiple doses of an injectable medicinal product and to dispense the set dosage of the product and to apply said product to a patient, preferably by injection. In particular, the present invention relates to such devices, which are handled by the patients themselves.

BACKGROUND

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reducible, the device should be inexpensive to manufacture and easy to dispose. In order to meet these requirements, the number of parts and steps required to assemble the device and an overall number of material types the device is made from have to be kept to a minimum.

Typically, the medicinal product to be administered is provided in a cartridge that has a moveable piston or bung mechanically interacting with a piston rod of a drive mechanism of the drug delivery device. By applying thrust to the piston in distal direction, a certain amount of the medicinal fluid is expelled from the cartridge.

Due to inevitable manufacturing tolerances there may for instance persist axial clearance between a cartridge's piston and the piston rod. Typically, prior to a primary use of the device, an end-user has to conduct a so-called priming of the drive mechanism in order to ensure, that already with an initial dose setting and a subsequent dose dispensing step, an accurate amount of the medicinal product is disposed in a predefined way.

Since a self-administering user might be physically infirm, it is desirable to simplify or even to eliminate the need for such a user-conductible priming procedure.

For instance, U.S. Pat. No. 6,196,999 B1 discloses a coupling mechanism, wherein a syringe plunger coupling element having the form of a rearwardly extending cylindrical extension is centrally located on a rearward face of a syringe plunger. This coupling element contains an interior T-shaped cavity, wherein the walls of said cavity are knurled to aid the grip of the coupling mechanism. The coupling mechanism is located on the forward end of a plunger drive ram proximate to the syringe plunger and is in the form of two pawls. These pawls are biased away from the plunger drive ram's axis of symmetry by means of springs. Operation of a motor advances the drive ram forwardly along its longitudinal axis to move the pawls of the coupling mechanism toward and inter engagement with the cylindrical extension of the syringe plunger.

As the advancing pawls initially enter the cavity of plunger extension, their forward ends are forced toward one another by the walls of the cavity, overcoming the outward bias of the springs. In order to eliminate an initial clearance between plunger and drive ram, the pawls have to fully enter the cavity to grip the knurled wall of the cavity. Henceforward, the syringe plunger and drive ram will move in a cooperated motion.

Document WO2009/095332 A1 further describes a way of minimizing a distance between a piston rod means and a plunger, wherein the piston rod means comprise a piston rod and a piston rod foot. The piston rod is provided with a number of protrusions engaging with a number of barbs on the piston rod foot. In this way it can be prevented, that the piston rod foot automatically separates from the piston rod. However, the relative position of piston rod foot and piston rod is governed by the positions of the mutually corresponding barbs and protrusions.

These known solutions feature the common drawback, that for elimination of axial clearance between piston rod and piston, the piston rod has to be axially shifted. Axial clearance- and backslash elimination implies to bring the piston rod in direct abutment position with a cartridge's piston. Such axial displacement of the piston rod for the purpose of clearance elimination is regarded as disadvantageous, because it typically involves a respective actuation of dose setting or dose dispensing means by the user.

It is therefore an object of the present invention to provide a drive mechanism for a drug delivery device featuring improved and facilitated clearance and manufacturing tolerance elimination. It is a further object of the invention to redundantize a priming procedure to be conducted by the user. The invention further focuses on improvements related to patient safety and intends to simplify the general device handling. It is a further object of the invention, to provide a drive mechanism for a drug delivery device with clearance eliminating means being inexpensive in production and being easy to assemble. Finally, it is an object of the invention to provide a method of eliminating clearance in a drive mechanism of a drug delivery device.

SUMMARY

In a first aspect, the invention provides a drive mechanism for a drug delivery device for dispensing of a dose of a medicinal product, typically a medicinal fluid, such as a fluid drug, e.g. insulin or heparin.

The drive mechanism comprises a holder for a product-containing cartridge, wherein the cartridge has a piston being slidably arranged therein in an axial direction. The drive mechanism further comprises a piston rod to be operably engaged with the cartridge's piston for dispensing of a well-defined dose of the medicinal product. With a distal outlet, the cartridge may be engaged with a needle, a cannula, an infusion tube or similar delivery devices in a fluid-transferring way. The cartridge itself may be designed as replaceable or disposable ampoule, carpule or syringe. Its piston is displaceable in distal direction for purging or expelling a pre-defined dose of medicinal product from the cartridge in an accurate way.

The drive mechanism further comprises an adjusting assembly, which is adapted to eliminate axial clearance between the piston of the cartridge and the piston rod of the drive mechanism. Such axial clearance may arise due to manufacturing or assembly tolerances of the drive mechanism, the drug delivery device and its various components. The adjusting assembly is further adapted to mutually lock into position the piston and the piston rod, irrespective of their relative distance or position. Hence, the adjusting assembly not only provides clearance- or backslash-elimination but also mutual interlocking of piston and piston rod.

The adjusting assembly further comprises at least one radially extending spike element or thorn-like prong. Said spike element or prong is adapted to establish a clamped or crimped-connection at least between the adjusting assembly and the piston rod. Typically, the adjusting assembly is arranged axially between piston and piston rod.

The adjusting assembly as a whole or its components typically provide a clearance-compensating function, e.g. by means of an axial movement relative to the piston and/or relative to the piston rod. Such axial movement of the adjusting assembly or its components is predominately governed by the amount of clearance to be eliminated, typically in the course of assembly of the drive mechanism or during assembly of the drug delivery device. As soon as a final, clearance-free assembly position has been reached, the adjusting assembly is typically immobilized with respect to the piston rod and/or with respect to the piston by means of the at least one radially extending spike element.

If the piston and the corresponding piston rod are mutually locked in position by the adjusting assembly, any axial movement, preferably any distally directed axial movement of the piston rod is directly and unalteredly transferred to the cartridge's piston. The axial movement of the adjusting assembly relative to the piston and/or relative to the piston rod may be conducted during or after assembly of the drive mechanism or the corresponding drug delivery device, respectively.

The adjusting assembly and/or its at least one spike element provide an at least unidirectional coupling of piston rod and piston. In this way, a cooperated movement of the piston and piston rod can be provided at least in distal direction. It is not generally required to have a bi-directionally coupled interlocking of piston and piston rod. In particular, in configurations with a re-usable drive mechanism, adjusting assembly and interlock means may allow the piston rod to be moved in proximal direction while the cartridge's piston remains stationary.

In a second aspect of the invention, the adjusting assembly comprises a receptacle being adapted to slidably receive a distal end section of the piston rod. Said distal end section of the piston rod is typically reduced in diameter and comprises a stepped down neck portion at its distal end. The receptacle comprises an axial extension allowing for a relative, clearance-compensating motion of piston and piston rod, in particular during assembly of the drive mechanism or during assembly of the drug delivery device, respectively. Preferably, the radial dimensions of the receptacle allow for an insertion of the receptacle into the cylindrical housing of the cartridge, e.g. in the course of subsequent dose dispensing procedures.

In typical embodiments, the receptacle of the adjusting assembly is pre-assembled to the distal neck portion of the piston rod. During assembly of the drive mechanism and/or the drug delivery device, said receptacle may abut against a proximal and thrust receiving face of the piston. Due to such an abutment, the receptacle may become subject to an axial displacement with respect to the piston rod until the housing is operably coupled with the cartridge holder. When this final assembly configuration has been reached, the receptacle is actively immobilized with respect to the drive mechanism's piston rod by making use of the at least one spike element. In this way, the piston of the cartridge becomes operably engaged with the piston rod.

According to a further preferred embodiment of the invention, the at least one spike element or the at least one thorn-like prong is adapted to pierce the piston rod. Alternatively or additionally, said spike element or prong may further be adapted to pierce a sidewall of the receptacle in radial direction. By means of the spike element or prong, the piston rod and the receptacle can be mutually locked in almost any arbitrary position within certain axial limits being governed by the size of the receptacle.

By way of the at least one spike element, preferably by means of several spike elements, a mechanical coupling of piston rod and piston being rigid in compression can be provided, wherein the relative axial position and distance of piston and piston rod may vary. Any manufacturing and/or assembly tolerances can therefore be compensated by the adjusting assembly according to the present invention.

According to a further preferred embodiment, the receptacle and the piston rod are mutually spring-biased in axial direction. Preferably, a spring element is disposed between a bottom face of the receptacle and a distal end face of the piston rod. Said spring element is preferably of compression spring type and allows for a spring-biased axial displacement of the receptacle relative to the piston rod. Making use of such a compression spring is beneficial during final assembly of the drive mechanism or the drug delivery device, respectively.

In a pre-assembly configuration, in which the receptacle is slidingly displaced on the distal neck portion of the piston rod, piston rod and piston of the cartridge can vary in position with respect to each other during the final assembly procedure. By way of the spring element being disposed between piston rod and bottom face of the receptacle, a compensating axial motion of piston rod and receptacle can be reached. The spring element provides axial bias between piston and piston rod even prior to a mutual interlocking of receptacle and piston rod. Also, by way of the spring element, any unintentional sliding displacement of receptacle and piston rod can be effectively compensated.

In a further preferred embodiment, the sidewall of the receptacle comprises axially extending slits, that divide the sidewall in at least two bendable sidewall sections. Typically, the sidewall of the receptacle is of tubular or cylindrical shape. Said axially extending slits extend to a proximal end section of the receptacle. In this way, the resulting sidewall sections are mutually disengaged at the receptacle's proximal end section towards the piston rod and the drive mechanism.

In a further preferred embodiment, the adjusting assembly comprises a fixing ring encircling or encompassing the receptacle in circumferential direction. The fixing ring is further slidably disposed along the receptacle's outer cylindrical surface. In this way, and in particular by shifting the fixing ring in proximal direction, any bendable sidewall sections of the receptacle's sidewall can be bended or pivoted radially inwardly in order to activate immobilization and interconnection of piston rod and receptacle, respectively. Preferably, the bendable sidewall sections of the receptacle's sidewall are biased in a radially outwardly pointing direction, in which a relative axial displacement of receptacle and piston rod is possible.

By means of axially moving the fixing ring in a locking position, the radial distance of the sidewall section's free ends is narrowed down and reduced and the radially extending spike elements engage with their respective counterpart in order to provide an interlocking of piston rod and receptacle.

In a further preferred embodiment, the fixing ring is slidably moveable in a locking position, in which the at least one spike element and the fixing ring substantially overlap in radial direction. In this way, the receptacle and the piston rod can be persistently mutually interlocked. The fixing ring serves as radial constriction for the receptacle's various sidewall sections and prevents radially outwardly directed bending of the sidewall sections, which may otherwise lead to a disengagement of receptacle and piston rod.

According to a further preferred embodiment of the invention, the at least one radially inwardly pointing spike element or a comparable thorn-like prong is disposed at a proximal end face of the receptacle. Typically, the spike element is disposed at a free end portion of each sidewall section of the receptacle's sidewall. Upon a proximally directed sliding of the fixing ring along the receptacle's sidewall sections, the free ends of the sidewall sections are forced radially inwardly, so that in effect the spike elements penetrate the piston rod.

According to another preferred embodiment of the invention, alternatively or additionally, the at least one spike element point radially outwardly and is disposed at the outer circumference of a distal portion of the piston rod. In this configuration, the sidewall sections of the receptacle's sidewall may comprise a rather straight and even contoured surface. An interconnecting piercing can in fact be achieved by a comparable proximally directed sliding motion of the fixing ring.

If arranged at the sidewall sections of the receptacle, the spike elements typically point radially inwardly. If arranged at the piston rod, said spike elements point radially outwardly in order to pierce and/or to penetrate the bendable sidewall sections of the receptacle.

In a further embodiment, the spike elements point radially outwardly. They are further arranged on a spiked ring, which is to be disposed in an annular groove of the piston rod. The spiked ring can for instance be adapted as clamping collar, in particular for the purpose of fixing the spiked ring to the piston rod. The spiked ring with its radially outwardly pointing spikes or prongs can be made of metal whereas the receptacle to be pierced by the spike elements is typically designed and manufactured as injection moulded plastic component.

Generally, the adjusting assembly provides mutual interlocking of the piston rod and the receptacle. The clamping achievable by the spike element can be of irreversible or reversible type. For instance, by removing the fixing ring or by displacing and returning the fixing ring in its initial distal position, a radial clamping can be reduced or even entirely suspended.

In another independent aspect a drug delivery device for dispensing of a pre-defined dose of a medicinal product is provided comprising a drive mechanism as described above. The drug delivery device is further equipped with a cartridge filled with the medicinal product to be dispensed. The cartridge typically comprises a cylindrical barrel filled with the medicinal product and is sealed in proximal direction with a displaceable piston which is to be displaced in distal direction for expelling a pre-defined amount of the medicinal product. The device may be of reusable and/or disposable type. Preferably, the device is to be commercially distributed with a filled cartridge readily disposed therein.

According to a further independent aspect, the invention provides a method of eliminating clearance between a piston and a piston rod of a drive mechanism of a drug delivery device. The drug delivery device or the drive mechanism comprises a holder for a product-containing cartridge. The cartridge comprises a piston being slidably arranged therein in an axial direction. The piston rod of the drive mechanism is to be operably engaged with the cartridge's piston for dispensing of a predefined dose of the medicinal product.

Said method of eliminating clearance or backslash during or after assembly of the drive mechanism or the drug delivery device comprises the steps of pre-assembling a cupped receptacle on a distal end section of the piston rod. The cupped receptacle is preferably spring-biased with respect to the piston rod and is therefore slidingly supported on the piston rod's distal end section. In this pre-assembled configuration, the housing of the drive mechanism and the cartridge holder are mutually assembled in a final assembly procedure. Typically, the housing is operably engaged with the drive mechanism and the cartridge is positioned and arranged in the cartridge holder.

In the course of final assembly, the piston rod is axially displaced in distal direction at least until the receptacle abuts against a proximal end face of the piston. Typically, the spring element sandwiched between receptacle and piston rod allows for a tolerance compensating mutual displacement of piston rod and piston. It may also allow for a respective mutual displacement of the housing and the cartridge holder of the drug delivery device. Irrespective of their relative position and distance, receptacle and piston rod are mutually locked in position by means of at least one radially extending spike element. For the purpose of mutually interlocking, said spike element or its counterpart, e.g. a bendable sidewall section of the receptacle, is displaced and/or pivoted in radial direction, wherein such radially directed displacement is typically supported by an axial and proximally directed displacement of a sliding ring.

The term "medicament" or "medicinal product", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the art, that various modifications and variations can be made to the present invention without departing from its spirit and scope. Further,

BRIEF DESCRIPTION OF THE DRAWINGS

Without limitation, the present invention will be explained in greater detail below in connection with preferred embodiments and with reference to the drawings in which:

FIG. 4 shows a perspective and cross-sectional illustration of a second embodiment of the present invention, FIG. 5 shows the drive mechanism according to FIG. 4 in an exploded view, and FIG. 6 schematically depicts the mutual interlocking of piston rod and receptacle according to FIGS. 4 and 5 in an enlarged illustration.

DETAILED DESCRIPTION

Figure 1:
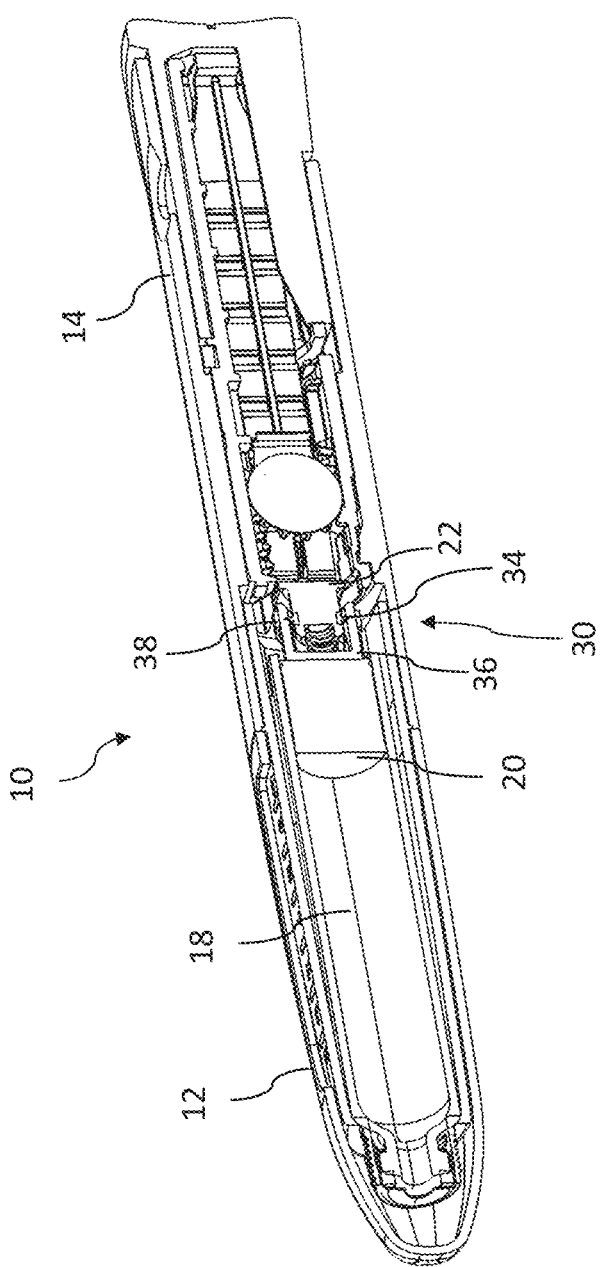
FIG. 1 shows a perspective cross-sectional side view illustration of a drive mechanism according to the present invention.
Figure 2:
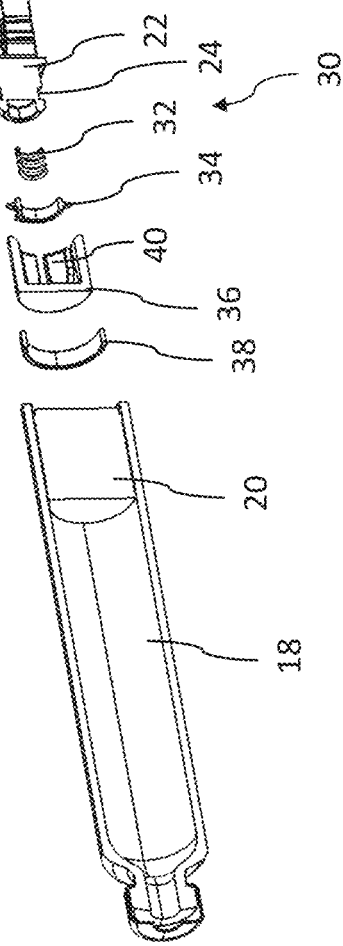
FIG. 2 illustrates the drive mechanism according to FIG. 1 in an exploded view.
Figure 3:
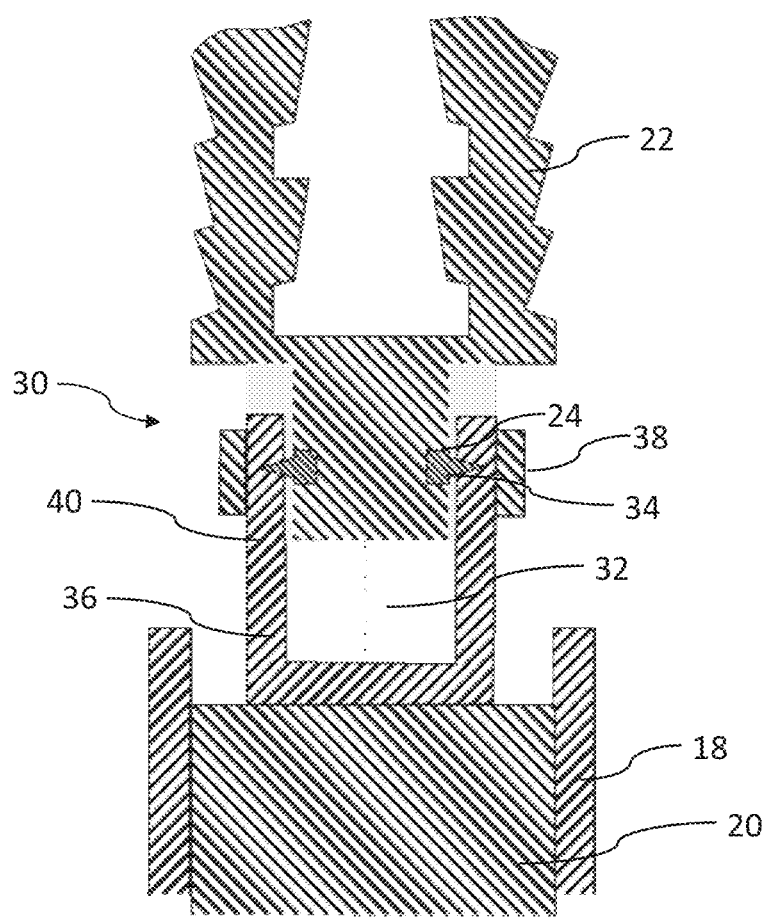
FIG. 3 shows the mutual interlocking of receptacle and piston rod according to FIGS. 1 and 2 in an enlarged illustration.

In FIGS. 1 to 3, a first embodiment of the drive mechanism 16 of a drug delivery device 10 of the present invention is illustrated. The drug delivery device of pen-injector type comprises a cartridge holder 12 at its distal end section and a housing 14 at its proximal end section. The cartridge holder 12 receives a disposable or replaceable cartridge 18 positioned inside the cartridge holder 12 as depicted in FIG. 1. In FIGS. 1 and 2, at its proximal, right hand side, the cartridge 18 has an axially slidably arranged piston 20, which—under an impact of a distally directed movement of a driven piston rod 22—is stepwise moved in distal direction for the purpose of expelling or purging a predefined amount of the medicinal product contained in the cartridge 18.

Cartridge holder 12 and housing component 14 are arranged in an interleaved manner, wherein a stepped down neck portion of either cartridge holder or housing is received in a corresponding receptacle of housing or cartridge holder, respectively.

A tolerance and clearance compensating adjusting assembly 30 provides an at least unidirectional engagement of piston rod 22 and piston 20. As illustrated in FIG. 3 in detail, the piston rod 22 comprises a stepped down neck portion at its distal end, which is received by a corresponding receptacle 36. In a pre-assembly configuration, the receptacle 36 is slidably attached to the distal end section of the piston rod 22. As illustrated in FIG. 2, the receptacle 36 further comprises a number of bendable sidewall sections 40 separated by axial slits. In this way, the sidewall of the receptacle 36 is radially expandable in proximal direction so as to receive radially outwardly pointing spike elements 34 arranged at the outer circumference of the piston rod's 22 distal end section.

A distal end face of the piston rod 22 and an inner bottom face of the receptacle 36 are mutually biased by a compression spring element 32. In this way, the receptacle 36 can be axially adjusted and aligned in the course of a final assembly procedure. The cylindrical receptacle 36 and its radially outwardly bendable sidewall sections 40 are encompassed by a fixing ring 38, which is slidably disposed at the outer circumference of the receptacle 36.

As soon as in the course of a final assembling procedure an abutment position of receptacle 36 and thrust receiving end face of the piston 20 has been reached, which is e.g. accompanied by a respective compression of the spring element 32, the fixing ring 38 is moved in proximal direction, thereby forcing the bendable sidewall sections 40 of the receptacle 36 radially inwardly, so that the sidewall sections 40 become pierced by the radially outwardly protruding spike elements 34 of the piston rod 22. The fixing ring 38 in its final assembly position as depicted in FIG. 3 substantially overlaps with the spike elements 34 in radial direction, thereby preventing unintentional disassembly of receptacle 36 and piston rod 22.

As further illustrated in FIGS. 2 and 3, the spiked ring 34 is disposed in an annular groove 24 of the piston rod 22. In this way, a reliable and easy to assemble fastening of spiked ring 34 and piston rod 22 can be achieved.

Figure 6:
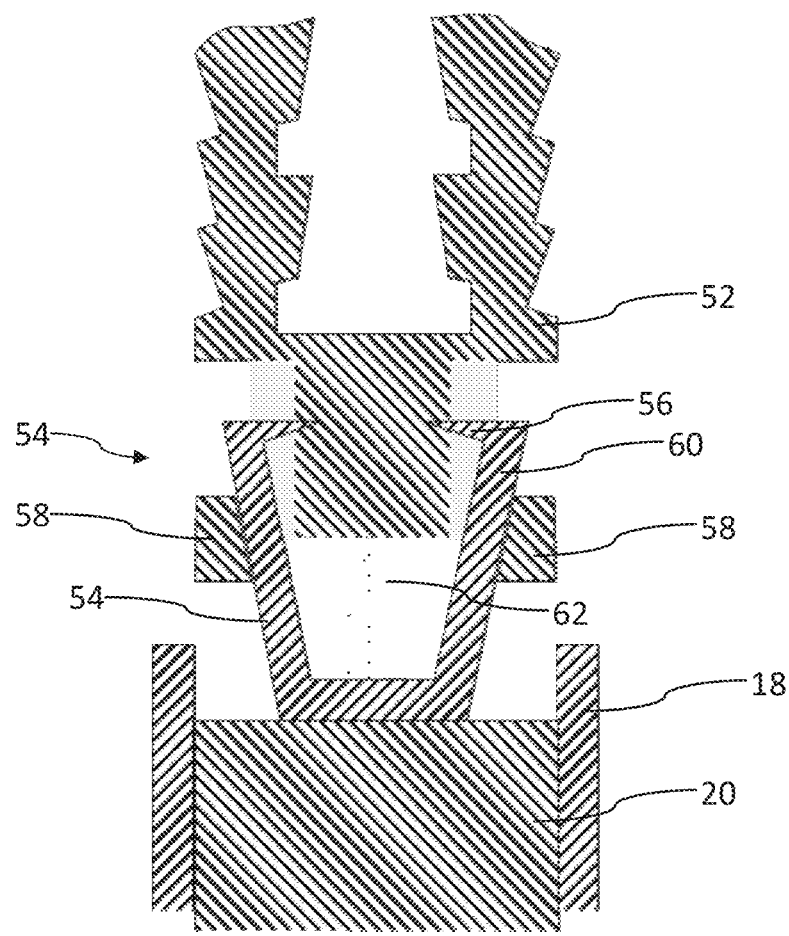

In FIGS. 4 to 6, a further embodiment of the invention is illustrated. Also this drug delivery device 50 comprises a drive mechanism 66 featuring an adjusting assembly 68 for compensating tolerances. In comparison to the embodiment according to FIGS. 1 to 3, the radially extending spike elements 56 are disposed at free end sections of the bendable sidewall sections 60 of the receptacle 54. Also here, a distal stepped down neck portion of the piston rod 52 is slidably received in the receptacle 54. Furthermore, the bottom portion of the receptacle 54 and a distal end face of the piston rod 52 are biased by a spring element 62.

In FIG. 6, an intermediate position of the bendable sidewall sections 60 and the fixing ring 58 is illustrated. By shifting the fixing ring 58 in proximal direction towards the piston rod 52, the sidewall section 60 will further bend radially inwardly, thus leading to a further penetration of the piston rod 52 by the radially inwardly protruding spike elements 56. Shifting the fixing ring 58 in the opposite, hence distal direction, the various sidewall sections 60 of the receptacle 54 may radially widen and may thus release the piston rod 52.

The invention claimed is:

1. Drive mechanism for a drug delivery device for dispensing of a dose of a medicinal product, comprising:
    a holder for a product-containing cartridge, the cartridge having a piston slidably arranged therein in an axial direction,
    a piston rod to be operably engaged with the cartridge's piston for dispensing of a dose of the medicinal product,
    an adjusting assembly adapted to eliminate axial clearance between the piston and the piston rod, characterized in that the adjusting assembly comprises a receptacle adapted to slidably receive a distal end section of the piston rod and further comprises at least one radially extending spike element adapted to pierce the piston rod and/or to pierce a side wall of the receptacle for mutually locking in position the piston and the piston rod irrespective of the relative distance between piston and piston rod.

2. The drive mechanism according to claim 1, wherein the receptacle, in a final assembly configuration, abuts against a thrust receiving proximal surface of the piston.

3. The drive mechanism according to claim 1, wherein the receptacle and the piston rod are mutually spring biased in distal direction.

4. The drive mechanism according to claim 3, wherein a spring element is disposed between a bottom face of the receptacle and a distal end face of the piston rod.

5. The drive mechanism according to claim 1, wherein the side wall of the receptacle comprises axially extending slits dividing the side wall in at least two bendable side wall sections.

6. The drive mechanism according to claim 2, wherein a fixing ring encompassing the receptacle in circumferential direction is slidably disposed along the receptacle's outer cylindrical surface.

7. The drive mechanism according to claim 6, wherein for mutually locking in position of receptacle and piston rod, the fixing ring is slidably movable in a locking position, in which the at least one spike element and the fixing ring substantially overlap in radial direction.

8. The drive mechanism according to claim 1, wherein at least one radially inwardly pointing spike element is disposed at a proximal end face of the receptacle.

9. The drive mechanism according to claim 1, wherein at least one radially outwardly pointing spike element is disposed at the outer circumference of a distal portion of the piston rod.

10. The drive mechanism according to claim 1, wherein a spiked ring comprising numerous radially outwardly pointing spike elements is arranged in an annular groove of the piston rod.

11. A drug delivery device dispensing of a pre-defined dose of a medicinal product comprising a drive mechanism according to claim 1 and further comprising a cartridge filled with the medicinal product to be dispensed.

* * * * *